United States Patent
Kumar et al.

(10) Patent No.: US 10,272,053 B2
(45) Date of Patent: *Apr. 30, 2019

(54) NANOPARTICLE TARGETED DRUG DELIVERY TO THE LUNGS USING EXTRA-TESTICULAR SERTOLI CELLS

(71) Applicants: Arun Kumar, Wesley Chapel, FL (US); Shyam S. Mohapatra, Lutz, FL (US); Don F. Cameron, Lutz, FL (US)

(72) Inventors: Arun Kumar, Wesley Chapel, FL (US); Shyam S. Mohapatra, Lutz, FL (US); Don F. Cameron, Lutz, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 445 days.

This patent is subject to a terminal disclaimer.

(21) Appl. No.: 14/879,649

(22) Filed: Oct. 9, 2015

(65) Prior Publication Data

US 2016/0089344 A1    Mar. 31, 2016

Related U.S. Application Data

(63) Continuation of application No. 12/918,265, filed as application No. PCT/US2009/001139 on Feb. 23, 2009, now Pat. No. 9,161,901.

(60) Provisional application No. 61/030,434, filed on Feb. 21, 2008.

(51) Int. Cl.
| | |
|---|---|
| A61K 31/12 | (2006.01) |
| A61B 5/00 | (2006.01) |
| A61K 9/00 | (2006.01) |
| A61K 9/50 | (2006.01) |
| A61K 9/51 | (2006.01) |
| A61K 47/36 | (2006.01) |
| A61K 47/46 | (2006.01) |
| A61K 49/00 | (2006.01) |
| B82Y 5/00 | (2011.01) |
| C12N 5/071 | (2010.01) |
| A61K 47/61 | (2017.01) |
| A61K 47/69 | (2017.01) |

(52) U.S. Cl.
CPC ............ *A61K 31/12* (2013.01); *A61B 5/0071* (2013.01); *A61B 5/4848* (2013.01); *A61K 9/0019* (2013.01); *A61K 9/5068* (2013.01); *A61K 9/5161* (2013.01); *A61K 47/36* (2013.01); *A61K 47/46* (2013.01); *A61K 47/61* (2017.08); *A61K 47/6901* (2017.08); *A61K 47/6939* (2017.08); *A61K 49/0043* (2013.01); *A61K 49/0093* (2013.01); *A61K 49/0097* (2013.01); *B82Y 5/00* (2013.01); *C12N 5/0683* (2013.01)

(58) Field of Classification Search
None
See application file for complete search history.

(56) References Cited

U.S. PATENT DOCUMENTS

| 5,474,989 A | 12/1995 | Hashimoto et al. |
|---|---|---|
| 5,759,534 A | 6/1998 | Selawry |
| 5,843,430 A | 12/1998 | Selawry |
| 5,849,285 A | 12/1998 | Selawry |
| 6,149,907 A | 11/2000 | Selawry |
| 6,649,192 B2 | 11/2003 | Alonso Fernandez et al. |
| 2007/0065422 A1 | 3/2007 | Cameron et al. |

FOREIGN PATENT DOCUMENTS

| WO | WO 1997/047323 | 12/1997 |
|---|---|---|
| WO | WO 2001/015669 | 3/2001 |

OTHER PUBLICATIONS

Selawry, H.P., et al., "Sertoli cell-enriched fractions in successful islet cell transplantation," *Cell Transplantation*, Mar./Apr. 1993, vol. 2, No. 2, pp. 123-129.

Xiaotao, Q., et al., "Enantioselective effects of experimental diabetes mellitus on the metabolism of ibuprofen," *Journal of Pharmacology and Experimental Therapeutics*, Sep. 1995, vol. 274, pp. 1192-1198.

Zhang, H., et al., "Monodisperse chitosan nanoparticles for mucosal drug delivery," *Biomacromolecules*, Nov. 2004, vol. 5, No. 6, pp. 2461-2468.

Corkery, K., "Inhalable drugs for systemic therapy," *Respiratory Care*, 2000, vol. 45, No. 7, pp. 831-835.

O'Riordan, T. et al. "Aerosol deposition in mechanically ventilated patients. Optimizing nebulizer delivery" *Am. J. Respir. Crit. Care Med.*, 1994, vol. 149, pp. 214-219.

Lalor, C.B., et al., "Generation and Characterization of Aerosols for Drug Delivery to the Lungs" in *Inhalation Delivery of Therapeutic Peptides and Proteins*, Akwete L. Adjei and Pramod K. Gupta, editors, Lung Physiology Series, Claude Lenfent, M.D., Series Editor, Marcel Dekker Publishers, 1997, pp. 235-276.

(Continued)

*Primary Examiner* — Taeyoon Kim
*Assistant Examiner* — Tiffany M Gough
(74) *Attorney, Agent, or Firm* — Saliwanchik, Lloyd & Eisenschenk (57) ABSTRACT

A method of delivering a compound of interest to the lungs of a subject by the intravenous injection of Sertoli cells loaded with a plurality of chitosan nanoparticles coupled with the compound of interest is provided. Testis-derived rat Sertoli cells were pre-loaded with chitosan nanoparticles coupled with or without the drug curcumin, pre-labeled with a fluorescent cell marker and then injected intravenously into the control or asthmatic mouse model host. Intact pre-loaded, pre-labeled Sertoli cells were present in the lungs at 15 minutes post-injection, appeared entrapped in the pulmonary pre-capillary vascular bed around alveolar sacs but were not present one hour post-injection although Sertoli cell label and cellular debris was. Most of the injected nanoparticle load (70%) and curcumin load (80%) was present in the lungs 15 minutes post-injection, and remained at 70% and 80%, respectively, one hour post-injection.

6 Claims, 7 Drawing Sheets

(56) References Cited

OTHER PUBLICATIONS

Edwards, D.A., et al. "Recent advances in pulmonary drug delivery using large, porous inhaled particles" *J. Appl. Physiol.*, 1998, vol. 85, pp. 379-385.
Venkatesan, N., et al., "Protection from acute and chronic lung disease by curcumin," *Advances in Experimental Medicine and Biology*, 2007, vol. 595, pp. 379-405.
Sowasod, N., et al., "Nanoencapsulations of Curcumin in biodegradable chitosan via multiple emulsion/solvent evaporation," *Thailand Materials Science and Technology Conference*, Apr. 1, 2006, pp. 1-3.
Grenha, A., et al., "Microencapsulated chitosan nanoparticles for lung protein delivery," *European Journal of Pharmaceutical Sciences*, 2005, vol. 25, pp. 427-437.
Amidi, M., et al., "Preparation and characterization of protein-loaded N-trimethyl chitosan nanoparticles as nasal delivery system," *Journal of Controlled Release*, 2006, vol. 111, pp. 107-116.
Bisht, S., et al., "Polymeric nanoparticle-encapsulated curcumin (nanocurcumin): a novel strategy for human cancer therapy," *Journal of Nanobiotechnology*, 2007, vol. 5, pp. 1-18.

NANOPARTICLE TARGETED DRUG DELIVERY TO THE LUNGS USING EXTRA-TESTICULAR SERTOLI CELLS

CROSS REFERENCE TO RELATED APPLICATIONS

The present application is a continuation of U.S. application Ser. No. 12/918,265, filed Apr. 20, 2011, which is the National Stage of International Application No. PCT/US2009/001139, filed Feb. 23, 2009, which claims the benefit of U.S. Provisional Application Ser. No. 61/030,434, filed Feb. 21, 2008, which is incorporated herein by reference.

BACKGROUND OF THE INVENTION

Drug delivery to diseased organs, such as the lungs, is challenging especially when the delivery of disease-effective therapeutics is limited, obstructed, or when there is a need to insure location-specific distribution of the drug. Pulmonary delivery of therapeutic drugs provides a number of benefits particularly with regard to absorption area and avoidance of first pass metabolism in the liver. However, meeting the sustained-release goal is somewhat problematic. The lungs tend to expel materials that are introduced and it is therefore difficult to keep the drug in the lung long enough for the sustained release to be effective. Additional challenges revolve around elimination of excipient (enabling delivery of a neat drug), elimination of Chlorofluorocarbon (CFC) propellants in Metered Dose Inhalers (MDI), reduction of the stigma associated with inhalers, and ease of use. Although a natural and safe route, pulmonary delivery has its challenges. The key challenge is getting the drug to reach the deep lung. Historically, aerosol formulations have not been able to move the medication into the deep lung efficiently, and until recently, pulmonary drug delivery systems have been developed to dispense drugs to the airways only for local applications. MDIs, breath-activated dry powder inhalers (DPIs), liquid jet, and ultrasonic nebulizers have proved useful in the management of asthma, but such devices are not designed to deliver drugs into the deep lung. They are not practical for the delivery of most macromolecules because of their low system efficiency, low drug mass per puff, poor formulation stability for macromolecules, and poor dosing reproducibility (Kevin Corkery, Inhalable Drugs for Systemic Therapy, Respir. Care. 45(7), 831-835 (2000)). Studies have established that these particles should range from 1 to 3 µm in diameter for optimal deposition efficiency. Most existing aerosol systems can deliver only a small fraction (about 10-20%) of the dispensed drug in the correct particle size for lung deposition. Furthermore, the amount of drug deposited from the device is highly dependent on the patient's inhalation technique. Any truly effective delivery device for proteins and peptides needs to optimize a patient's ability to inhale correctly (O'Riordan T. G., Palmer, L. B., & Smaldone, G. C. Aerosol deposition in mechanically ventilated patients. Optimizing nebulizer delivery, Am. J. Respir. Crit. Care Med. 149, 214 (1994)).

Most aerosol systems today deliver a total amount of <100 µg of drug per puff to the deep lung; this amount is too low to enable timely delivery of many macromolecules for the required milligram-level doses. Any aerosol system developed for large molecules will have to exhibit a characteristic that is called "payload versatility," that is, the ability to deliver varying amounts of a drug. Payload versatility will be necessary because the new macromolecule drugs vary widely in potency from a few micrograms to tens of milligrams per dose. Traditional inhalation systems have been designed primarily to deliver some of the most potent drugs in use today, the bronchodilators and bronchosteroids to treat asthma. Both types of compounds are bioactive in the lung at 5-20 µg per dose. In contrast, many peptide and protein compounds need to be delivered to the deep lung at much larger doses of 2-20 mg (Inhalation Delivery of Therapeutic Peptides and Proteins, Akwete L. Adjei and Pramod K. Gupta, editors, Lung Physiology Series, Claude Lenfent, M. D., Series Editor, Marcel Dekker Publishers, 1997; Generation and Characterization of Aerosols for Drug Delivery to the Lungs C B Lalor, A J Hickey—Lung Biology In Health And Disease, 1997—Marcel Dekker Ag).

For inhalation therapies to accomplish their medical goals, macromolecule delivery to the lungs must be precise and consistent at every inspiration. Although the natural bioavailability of the deep lung epithelia appears difficult to change, the efficiency of drug deposition can be improved by utilizing permeation enhancers such as surfactants, fatty acids, and saccharides; and chelating agents and enzyme inhibitors such as protease inhibitors. (Edwards D. Al, Ben-Jebria, A., & Langer, R. Recent advances in pulmonary drug delivery using large, porous inhaled particles. *J. Appl. Physiol.* 85, 379-385 (1998)). Deposition efficiency from traditional devices, however, remains low with less than 10% of the total inhaled dose reaching the deep lung.

Chitosan nanoparticles have been used to deliver drugs nasally as a therapeutic treatment protocol for asthma and COPD. Although effective medically, delivery of drug-containing nanoparticles through the air way is difficult when there are obstructive airway issues. Nanoparticle delivery is poor (10-30%) and distribution in this way is difficult to control resulting in sub-optimal efficiency.

SUMMARY OF INVENTION

The invention includes a method of delivering a compound of interest to the lungs of a subject by the intravenous injection of Sertoli cells loaded with a plurality of chitosan nanoparticles coupled with the compound of interest. Testis-derived rat Sertoli cells were pre-loaded with chitosan nanoparticles coupled with or without the drug curcumin, pre-labeled with a fluorescent cell marker and then injected intravenously into the control or asthmatic mouse model host. Intact pre-loaded, pre-labeled Sertoli cells were present in the lungs at 15 minutes post-injection, appeared entrapped in the pulmonary pre-capillary vascular bed around alveolar sacs but were not present one hour post-injection although Sertoli cell label and cellular debris was. Most of the of the injected nanoparticle load (70%) and curcumin load (80%) was present in the lungs 15 minutes post-injection, and remained at 70% and 80%, respectively, one hour post-injection.

Following Sertoli cell lyses in the lungs, curcumin-coupled nanoparticle delivery was achieved based on the absence of intact Sertoli cells, the positive assay for both nanoparticles and curcumin, and the therapeutic effects achieved in the lungs following Sertoli cell injection. Results identify a new and efficient protocol for targeted delivery of drugs to the lung mediated by extra-testicular Sertoli cells which may optimize the drug therapy for asthma and COPD and possibly other lung diseases such as lung cancer.

BRIEF DESCRIPTION OF THE DRAWINGS

For a fuller understanding of the invention, reference should be made to the following detailed description, taken in connection with the accompanying drawings, in which:

FIG. 1A is an image of Sertoli cells in in vitro exposed to FITC-labeled nanoparticles. Plated Sertoli cells, viewed through the FITC filter, contain nanoparticles whereas the contaminating peritubular cells do not indicate selective phagocytose by the Sertoli cells.

FIGS. 2A through 2C are a series of images of Sertoli cells in vitro pre-loaded with FITC-labeled (green) nanoparticles and pre-labeled with DiI (red). In FIG. 2A, suspended Sertoli cells are imaged by DIC which in FIG. 2B fluoresce red when viewed though the TRITC. When viewed through the FITC filter. FIG. 2C intact pe-loaded, pre-labeled Sertoli cells appear yellow.

FIGS. 4A-4D Mouse lung 1 hour following injection of pre-loaded, pre-labeled rat Sertoli cells imaged by florescence microscopy (A-C) and by electron microscopy (D). Lungs were removed from the injected mouse (exp) and from an un-injected control mouse (con), positioned together on the microscope and visualized using the Olympus AX100 super stereo scope by bright field microscopy (A) and by florescence microscopy through a TRITC filter (B) and though a FITC filter (C). Homogenous Sertoli cell label (red) and nanoparticle label (green) are evident in the 1 hour lung but none in the control lung. Insets: (B) and (C) are croysections from a mouse lung collected 15 minutes post-injection in which Sertoli cell label is evident (insert B, red). The label represents intact pre-loaded, pre-labeled Sertoli cells (insert c, yellow). Intact cells are not apparent in the 1 hour post-injection lung (C) as indicated by the absence of yellow fluorescence. In (D), a pulmonary capillary in the injected mouse, imaged by electron microscopy, contains what appears to be cellular debris (arrows) and aggregated labeled-nanoparticles (asterisk). Inset: Electron micrograph of labeled nanoparticles.

FIG. 5 Percent of the total delivered nanoparticles (detected at 493 nm, black bar) of rat Sertoli cells (detected at 553 nm, white bar) and curcumin (detected at 420 nm striped bars) in 1) pre-loaded, pre-labeled Sertoli cells alone ($8 \times 10^6$), 2-5) mouse organs collected 1 hour following injection of the pre-loaded, pre-labeled Sertoli cells and 6) lungs collected from un-injected mice. The percent of total injectable of Sertoli cells, nanoparticles and curcumin one hour post-injection was highest in the lungs (2) with minimal nanoparticle detection (black bars) in the liver (3) and kidneys (4) and none in the thymus (5) nor the un-injected control lungs. There was reduced detection of Sertoli cells (whitebars) in the mouse lungs 1 hour post-injection (2) and no detection of Sertoli cells in the liver (3), kidney (4), thymus (5) nor the un-injected control lungs (6). Curcumin detection one hour post-injection in the lungs of asthmatic mice (2, striped bar) represented a high percentage (80%) of the total amount of drug deliver by Sertoli cells.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The invention includes a method of delivering drugs to the lungs utilizing a biocompatible cell-based system designed to maximize drug volume and delivery, and more efficiently target the deep lung. In one embodiment, Sertoli cells isolated from the testis (i.e. extra-testicular Sertoli cells, $SC_{ET}$) have been used to facilitate cell transplantation therapy (Emerich D. F., Hemendinger, R., & Halberstadt, C. R. The testicular-derived Sertoli cell: cellular immunoscience to enable transplantation. *Cell Transplant*. 12, 335-349 (2003)). They provide for the immunoprotection of allo- and xenogeneic cell transplants and, themselves, avoid immune rejection (Emerich D. F., Hemendinger, R., & Halberstadt, C. R. The testicular-derived Sertoli cell: cellular immunoscience to enable transplantation. *Cell Transplant*. 12, 335-349 (2003); Sipone S, et al. Identification of a novel human granzyme B inhibitor secreted by cultured Sertoli cells. *J. Imunology*. 177, 5051-5058 (2006); Dufour J. M., Hamilton, M., Jajotte, R., & Korbutt, G. Neonatal procine Sertoli cells inhibithuman natural antibody-mediated lysis. Biol. Reprod. 72, 1224-1231 (2005)).

One reported mechanism by which $SC_{ET}$ immunoprotect cell grafts is the induction of donor specific tolerance in the host following intravenous (IV) injection of the $SC_{ET}$ (Shamekh R., Dagani, N., Saporta, S., Pascual, J., Sanberg, P. R. & Cameron, D. F. Sertoli cells induce systemic donor-specific tolerance in xenogenic transplantation model. *Cell Transplant*, 15; Kevin Corkery. Inhalable Drugs for Systemic Therapy. Respir. Care. 45 (7), 831-835 (2000)), 45-53 (2006)). The large $SC_{ET}$ (~30-50 µm) appear to become entrapped in the pre-capillary vascular bed of the lung, where the lysed cells are quickly cleared from the system without deleterious effects to the individual (Id).

The inventors found that the $SC_{ET}$ not only possessed aggressive phagocytic activity for chitosan nanoparticles, but also they readily entered the lung capillaries and delivered these nanoparticles when $SC_{ET}$ were injected via the venous vasculature. They reasoned that therapeutic nanoparticles can be delivered to the deep lungs by way of $SC_{ET}$ used as a carrier. Such delivery protocol can serve to overcome the limitations inherent in inhalation air way delivery protocols. The examples, below, describe the delivery of curcumin coupled nanoparticles to the lungs of normal mice and the asthmatic mouse model by the IV injection of extra-testicular Sertoli cells.

EXAMPLE 1

$SC_{ET}$ Cell Uptake of Chitosan Nanoparticles

Nanoparticles were prepared from chitosan (CS, Vanson Wash. 98052) having a molecular weight of 60,000±2183 Daltons by ionotropic gelation with negatively charged Tripolyphosphatesodium (TPP) ions according to a previously reported procedure (Zhang H., Oh, M., Allen, C., & Kumacheva, E. Monodisperse chitosan nanoparticles for mucosal drug delivery. *Biomacromolecules*, 5, 2461-2468 (2004)). Briefly, CS was dissolved in an aqueous solution of acetic acid at concentrations of 0.05, 0.10, 0.15, and 0.20 wt %. The concentration of acetic acid was 1.75 times as high as that of CS. For example, 0.10 wt % CS solution was prepared in 0.175 wt % acetic acid solution. Then, 1.0 mL of TPP (sodium tripolyphosphate) solution was added dropwise to 0.5 mL of CS solution in a 20-mL glass vial under magnetic stirring at 600 (20 rpm measured by a tachometer using an octagonal stirring bars). The mixture was stirred for an additional 10 minutes. The weight ratios of CS/TPP were 4:1, 4.5:1, 5:1, 5.5:1 and 6:1. At least five batches of CS NPs were obtained from each protocol.

Labeling Chitosan Nanoparticle with FITC or AlexaFluor™. Dehydrated methanol (100 mL), followed by 2.0 mg/mL of FITC (Fluorescein-C6-Amine Labeling Kit, PAN-VERA, Madison Wis.) or AlexaFluor (Molecular Probes) in methanol (50 mL), was added into 1% w/v chitosan hydrochloride in 0.1 M acetic acid solution (100 mL) with stirring at 1000 rpm at ambient temperature. After 3 hours of reaction in the dark at ambient temperature, the fluorescent-labeled chitosan was precipitated in 0.2 M NaOH and separated from unreacted labeled using dialysis membrane MWCO:12-14,000 with flat width of 45 mm with 1/15M phosphate buffer/0.2 M NaCl (pH 5.5) as elution solvent and dialyzed in 100 mL of distilled water for 3 days in the dark (Maryam A., Romeijn, S. G., Borchard, G., Junginger, H. E., Hennink, W. E., & Jiskoot, W. Preparation and characterization of protein-loaded N-trimethyl chitosan nanoparticles as nasal delivery system, *J. Control Release* 111(12), 107-116 (2006)). The labeled nanoparticles were characterized and used for uptake studies immediately upon preparation. Tripolyphosphatesodium (TPP), acetic acid, FITC or AlexaFluor, chlorpromazine, filipin, sucrose, Triton X-100, and methanol were purchased from Sigma Chemical Co. (St. Louis, Mo., USA), and dialysis membrane MWCO:12-14, 000 with flat width 45 mm was purchased from Spectrum Laboratories Inc. (CA, USA). The transport medium was composed of Hanks Balanced Salt Solution (HBSS), buffered with 10 mM N-2-hydroxyethylpiperazine-N'-2-ethanosulfonic acid (HEPES) and adjusted to pH 6.2 with 1.0 M HCl and purchased from Sigma. Ultrapurewater (Millipore, Bedford, Mass., USA). All other chemicals were of the highest grade available commercially.

Sertoli Cell Isolation, Preparation. Sertoli cells were isolated from prepubertal Sprague-Dawley rat testes by sequential enzymatic digestion as previously reported (Cameron D. F., & Muffly, K. E. Hormonal regulation of spermatid binding to Sertoli cells in vitro. *J. Cell Sci.* 100, 523-533 (1991)) and maintained in DMEM/F12 supplemented with insulin-transferrin-selenium (ITS, 0.1%, Sigma) and gentamicin sulfated (50 g/ml, Sigma). FITC- or Alexa Fluor-labeled (green) Chitosan nanoparticles 7 (0.5 mg/mL) 500 μL were added directly to the medium and incubated with the substrate adherent extra-testicular Sertoli cells ($SC_{ET}$) for 15 hours. The $SC_{ET}$ cultures were aggressively washed (5×) with medium to remove the unphagocytosed nanoparticles, lifted from the substrate with trypsin (0.25%/medium), washed (3×) and then pre-labeled with either the DiO (green, Molecular Probes) or DiI (red, Molecular Probes) fluorescent cell markers as previously reported (Golat B. & Cameron, D. F. Extra-testicular Sertoli cells enhance new capillary growth in vitro, *Cell Transplant* (2008)). Substrate adherent and suspended pre-loaded, pre-labeled $SC_{ET}$ were imaged utilizing the Olympus IX71 inverted florescent microscopy to verify nanoparticle phagocytosis and to define the pre-loaded, pre-labeled $SC_{ET}$ image profiles.

Figure 1A:
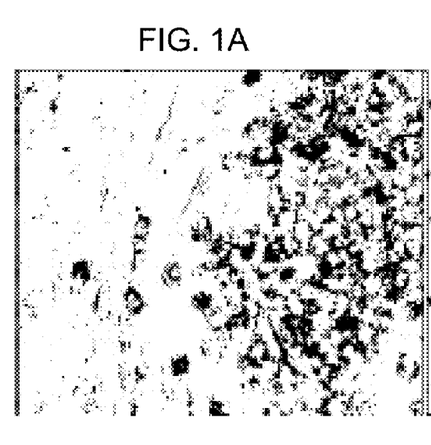
Figure 1B:
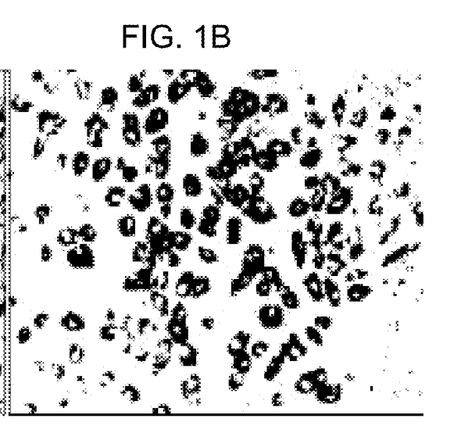
FIG. 1B is an image of Sertoli cells in in vitro exposed to FITC-labeled nanoparticles. The single cell suspension of nanoparticle pre-loaded Sertoli cells, as viewed through the FITC filter, are well identified by the green fluorescence generated by FITC-labeled nanoparticles.
Figure 2A:
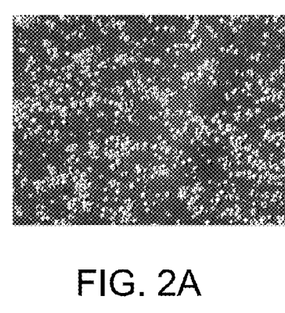
Figure 2B:
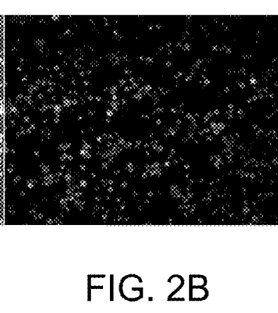
Figure 2C:
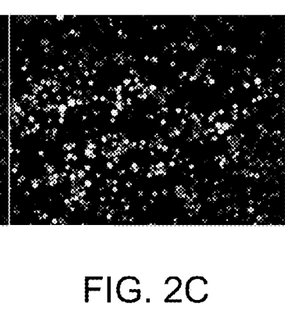

Isolated rat Sertoli cells (SCs), in primary cell culture, aggressively and selectively phagocytosed labeled nanoparticles as determined by label-specific positive cytoplasmic fluorescence in the SCs and the absence of fluorescence in contaminating peritubular cells (FIG. 1a). When in single cell suspension, these nanoparticle pre-loaded extra-testicular Sertoli cells ($SC_{ET}$) had cytoplasm that imaged bright green when viewed through the FITC filter (FIG. 1b). When the nanoparticles pre-loaded $SC_{ET}$ were subsequently pre-labeled with DiI (red), the cells imaged red when view through the TRITC filter (FIG. 2b) but imaged yellow when view through the FITC filter (FIG. 2c). These results show that $SC_{ET}$ cells take up nanoparticles readily.

EXAMPLE 2

Pre-loaded, Pre-labeled $SC_{ET}$ Enter into Deep Lung when IV Injected

Project Design, Animals, Tissue Collection and Morphological Evaluation. Pre-loaded, pre-labeled rat $SC_{ET}$ were injected (8×10$^6$) into recipient mice (C57BL/6 and BALB/c mice, Harlan and Jackson Laboratory) through the lateral tail vein in a total volume 150 μl culture medium. Tissues and organs were collected from intravenously (i.v.) transplanted mice (experimental) and un-injected mice (controls) 15 minutes, 1 hr and 24 hours post-injection. Controls included mice injected with $SC_{ET}$ only, $SC_{ET}$ pre-labeled with either DiI or DiO only, and $SC_{ET}$ containing only nanoparticles. Organs and tissues collected included the lungs, spleen, thymus, liver, kidneys, pancreas, muscle, blood and bone marrow. Some tissues were fixed with 4% paraformaldehyde/PBS for LM morphological evaluation, with 3% gluderaldehyde/PBS for TEM structural evaluation, some were flash frozen and cyosectioned for LM detection of fluorescence and some unfixed whole organs were prepared for the detection of florescence utilizing the Olympus AX100 florescence stereoscope.

Following IV injection of the pre-labeled $SC_{ET}$, spleen, liver, thymus, lung, kidney, muscle, pancreas, bone marrow and blood were removed from the euthanatized mouse hosts 15 minutes, one hour and 24 hours post-injection, fixed, and processed for the detection of fluorescence specific to the labeled $SC_{ET}$. There was no evidence of intact cells in any of the tissues collected except the lungs.

Figure 3A:
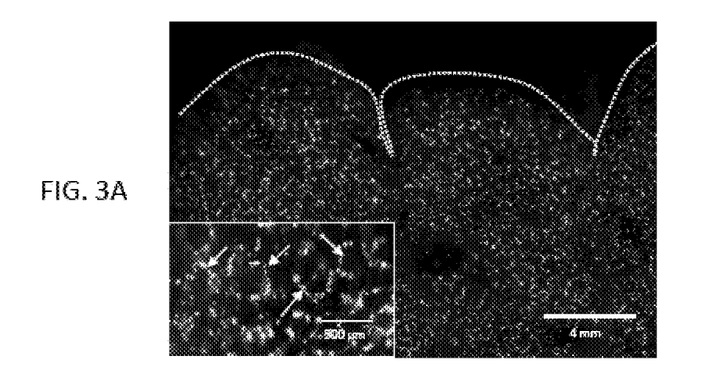
FIG. 3A is an unfixed whole mouse lung 15 minutes post-injection (IV) of DiO-labeled SCET (green) indicating a homogeneous distribution of the injected cells in the organ when A) viewed through the FITC filter.
Figure 3B:
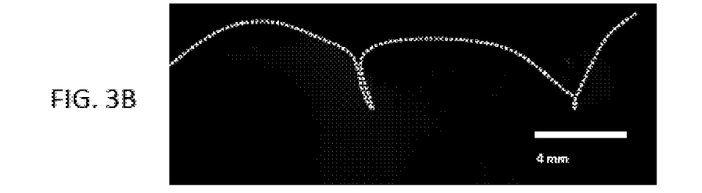
FIG. 3B is the same field of view imaged through the TRITC filter indicating label specific imaging in FIG. 3A. Inset: higher magnification of the lung in 3A shows to better advantage the distribution of labeled Sertoli cells around what appears to be the peri-alveolar sac vasculature (arrows).

At 15 minutes post-injection, fluorescence specific for pre-labeled $SC_{ET}$ (DiI, green) appeared homogeneous in the whole lung (FIG. 3). At higher magnification, $SC_{ET}$ appeared to be present in the peri-alveolar pre-capillary vasculature (FIG. 3a insert). In cryosections of unfixed lungs, intact pre-loaded, pre-labeled $SC_{ET}$ were evident as evidenced by yellow fluorescence when viewed thought the FITC filter (FIG. 4c insert).

Figure 4A:
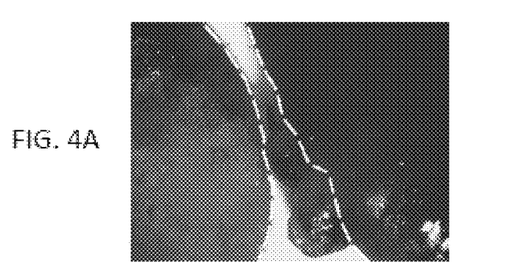
Figure 4B:
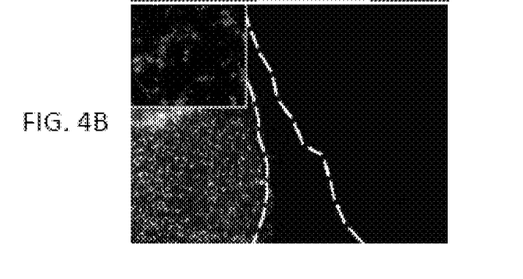
Figure 4C:
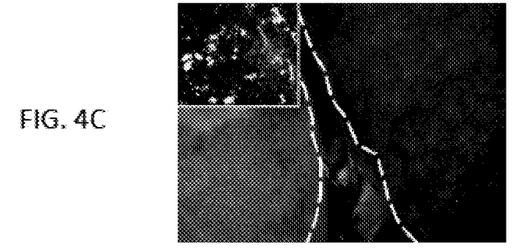
Figure 4D:
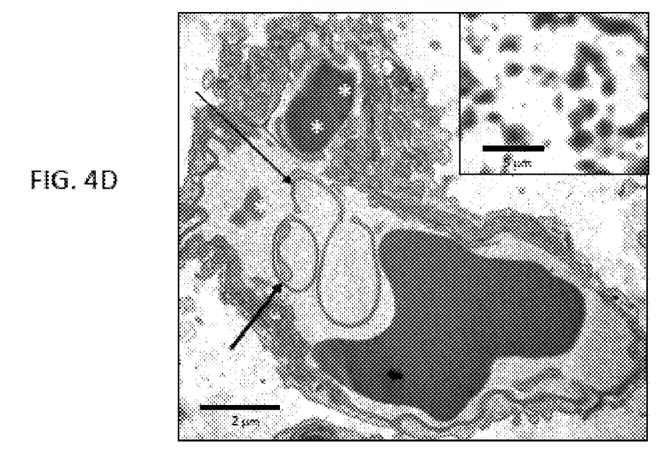

At one hour post-injection, whole lungs (FIG. 3a,b,c) imaged brightly for the Sertoli cell label (red) when view thought the TRITC filter (FIG. 3b), but there was no evidence of intact $SC_{ET}$ as evidenced by the absence of yellow fluorescent when viewed thought the FITC filter (FIG. 4c insert). When viewed through the FITC filter, there was a homogenous distribution of green fluorescence indicating positive detection for the AlexaFlour-labeled nanoparticles only (FIG. 4c). Tissue processed for electron microscopy from the one hour post-injection control lung appeared normal except that some small vessels and capillaries contained cell membrane debris and inclusions similar in appearance to aggregated labeled nanoparticles (FIG. 4d). These results provide evidence that the nanoparticle pre-loaded and pre-labeled $SC_{ET}$ readily appear at the lung capillaries and release the nanoparticles to the capillaries.

EXAMPLE 3

Absorption of Nanoparticle Conjugated Drugs in the Deep Lung

The aborption of nanoparticles and Sertoli Cells was quantified. Some lungs, thymus, liver and kidneys from experimental and control mice were homogenized and processed for the quantification of labeled nanoparticles by florescence absorbance assay performed at a fixed wavelength using UV spectrophotometer for FITC or AlexaFluor at 553 nm. Quantification of Sertoli cells in this tissue also was assayed by florescence absorbance performed at 493 nm for DiI. Controls included the quantification, by florescence absorbance assay, of native labeled nanoparticles, suspended pre-loaded $SC_{ET}$ ($10 \times 10^6$) alone and suspended pre-labeled $SC_{ET}$ ($10 \times 10^6$) alone.

To quantify uptake of Curcumin, the right lung of each mouse was collected 24 hours after the treatment injection. Each lung was placed in a labeled container with 1 ml PBS. The lungs were then sonicated for 10 seconds by the Sonic Dismembrinator 60 (Fisher Scientific) to lyse the Sertoli cells and release the curcumin nanoparticles. The curcumin was then separated from the nanoparticles by adding 500 µl DMSO to each container. The suspension was then centrifuged at 1200 rpm for 10 minutes and the supernatant was collected. A UV spectrum was collected from each supernatant sample.

Figure 5:
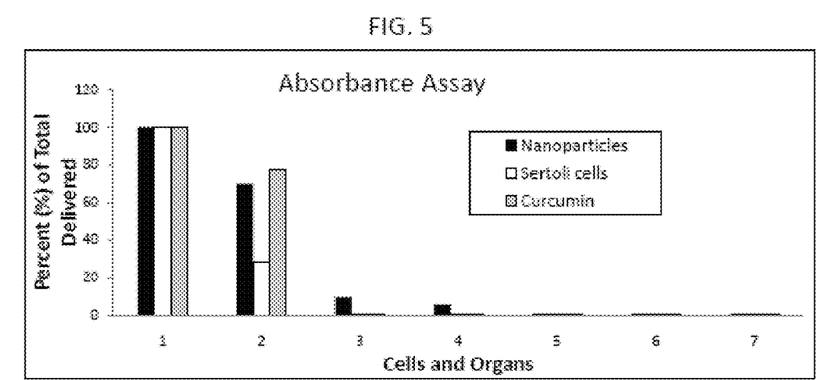

$SC_{ET}$ pre-loaded with AlexaFlour-labeled nanoparticles only, $SC_{ET}$ only pre-labeled with DiI, and pre-loaded, pre-labeled $SC_{ET}$ were assayed for fluorescence absorption at wave lengths specific for the nanoparticle label (AlexaFlour—493 nm or FITC—280 nm) and the Sertoli cell label (DiI, 553 nm). The number of cells homogenized and assayed ($8 \times 10^6$) was the same number as were injected into the mouse host. Specific absorption in arbitrary units from pre-loaded only $SC_{ET}$ was 4.5 (with FITC filter), from pre-labeled only $SC_{ET}$ was 4.7 (with TRITC filter), and from pre-loaded, pre-labeled $SC_{ET}$ was 3.5 (with the FITC filter) and 3.7 (with TRITC filter) (FIG. 5).

Tissues and organs collected from mice injected with pre-loaded, pre-labeled $SC_{ET}$ and from control un-injected normal mice were homogenized and assayed for label by specific wave length absorbance assay. No label was detected in all tissues assayed except the lungs, liver and kidneys collected from mice 15 minutes and 1 hour post-injection. Additionally, specific wave length absorbance for curcumin (AlexaFlour—493 nm or FITC—280 nm) was determined in lungs of mice injected with pre-labeled $SC_{ET}$ containing nanoparticles coupled with curcumin.

Fifteen minutes post-injection, mean specific absorbances of labeled nanoparticles in arbitrary units derived from normal mouse lungs 15 minutes post-injection was 3.8 from liver was 0.3 and from kidney was 0.2. Specific absorbances in the spleen and lungs from control mice were not detected. When expressed as the percentage of nanoparticles contained in the pre-loaded, pre-labeled $SC_{ET}$ injectable ($8 \times 10^6$), the lungs contained 69% of the total load, while the liver and the kidneys contained 5% and 7%, respectively (FIG. 5).

One hour post-injection, mean specific absorbances of labeled nanoparticles from normal mouse lungs one hour post-injection was 2.5 from liver was 0.4 and from kidney was 0.2. Specific absorbance from the spleen and lungs from control mice lungs was not detected. When expressed as the percentage of the total nanoparticles contained in the injected pre-loaded, pre-labeled $SC_{ET}$, the lungs contained 70% of the total load, while the liver and the kidneys contained 11% and 5%, respectively (FIG. 4). Mean specific absorbance of labeled $SC_{ET}$ in arbitrary units derived from normal mouse lungs one hour post-injection was 1.0, from liver was 0 and from kidney was 0. Specific absorbance from the spleen and lungs from control mice was not detected. When expressed as the percentage of the total number of $SC_{ET}$ injected, the lungs contained 26% of the total number, while the liver and the kidneys contained 0% and 0%, respectively (FIG. 5).

Curcumin was assayed in lungs derived from injected asthmatic mice 25 hours following the time of injection. Curcumin was not detected in un-injected asthmatic-mice lungs. When expressed as the percentage of the total amount of curcumin in the injected $SC_{ET}$, the lungs contained 80% of the total load.

EXAMPLE 4

$SC_{ET}$-delivered Curcumin Nanocomlexes Decrease Asthmatic Inflammation

In addition to normal mice, some female C57BL/6 and BALB/c mice were sensitized by intraperitoneal injection (i.p.) of 10 µl ovalbumin (OVA) with alum as previously described to mimic acute allergic asthma (Weggman, M. Animal models of chronic experimental asthma—strategies for the identification of new therapeutic targets. *Occup Med Toxicol*. 3 (Suppl 1) (2008); Temelkovski J, Hogan S P, Shepherd D P, Foster P S, Kumar R K. An improved murinemodel of asthma: selective airway inflammation, epithelial lesions and increased methacholine responsiveness following chronic exposure to aerosolised allergen. Thorax. 10, 849-56 (1998)). The mice were challenged weekly for 3 weeks with an intranasal injection (i.n.) of 25 µl OVA (20 mg/ml). One hour after the last i.n. challenge, the treatment group (n=7) was injected via the tail vein with pre-loaded, pre-labeled $SC_{ET}$ ($8 \times 10^6$) that contained nanoparticles coupled with 6.25 mg/µl curcumin dose. Others asthmatic mice were not injected with $SC_{ET}$ to serve as untreated controls (n=6). Lungs from treated and untreated control asmatic mice were collected 24 hours later evaluated morphologically and assayed for curcumin.

Figure 6A:
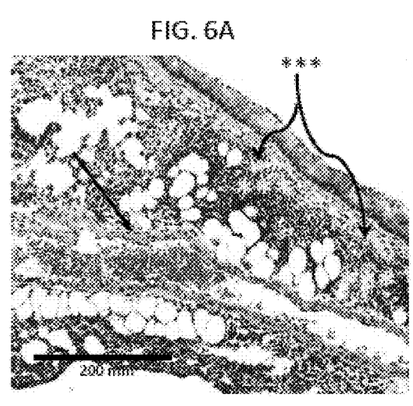
FIGS. 6A and 6B are examples of light microscopic images of sectioned lung tissues from (FIG. 6A) untreated mouse and (FIG. 6B) mouse injected with Sertoli cells pre-loaded with curcumin-laden nanoparticles. Lung tissue from the untreated mouse shows extensive perivascular inflammation as indicated by the presence of inflammatory cells (***). In all seven Sertoli cell injected mice, there was no evidence of pulmonary inflammation based on the absence of inflammatory cell types in the tissue, as illustrated in (FIG. 6B). Arrow=pulmonary blood vessel. H-E, 4 µm.
Figure 6B:
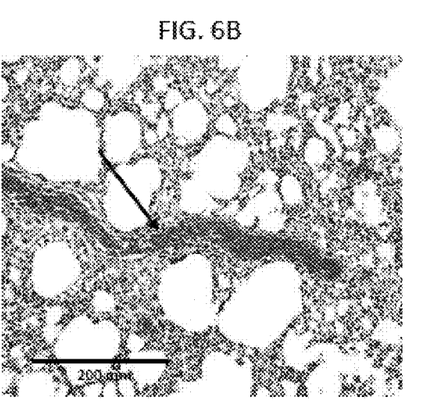

Histopathology of Curcumin-treated Asthmatic Mouse Lungs. Curcumin coupled nanoparticles were delivered, by i.v. injected $SC_{ET}$, to the lungs of asthmatic mice challenged with OVA to induce pulmonary inflammation. Lungs from the un-injected control mice presented with diffuse perivascular inflammatory cell invasion into the interstitial pulmonary space (FIG. 6a) as previously described. Lungs from all 7 asthmatic mice injected with $SC_{ET}$ pre-loaded with curcumin-coupled nanoparticles were clear of inflammatory pathology as judged by the absence of inflammatory cell types in the pulmonary tissue observed (FIG. 6b).

The right lung of each mouse was collected 24 hours after the treatment injection. Each lung was placed in a labeled container with 1 ml PBS. The lungs were then sonicated for 10 seconds by the Sonic Dismembrinator 60 (Fisher Scientific) to lyse the Sertoli cells and release the curcumin nanoparticles. The curcumn was then separated from the nanoparticles by adding 500 µl DMSO to each container. The suspension was then centrifuged at 1200 rpm for 10 minutes and the supernatant was collected. A UV spectrum was collected from each supernatant sample. Data was presented for absorbance assays of Sertoli cells, nanoparticles and curcumin from all samples from all mice, including a sample of the nanoparticle pre-loaded, pre-labeled SC injectable ($8\times10^6$) were replicated and the mean values of SCs, nanoparticles and curcumin were expressed as a percentage of the mean value determined in the pre-loaded, pre-labeled Sertloli cell injectable ($8\times10^6$)

Curcumin coupled nanoparticles were delivered, by i.v. injected of $SC_{ET}$, to the lungs of asthmatic mice challenged with OVA to induce pulmonary inflammation. Lungs from the un-injected control mice presented with diffuse perivascular inflammatory cell invasion into the interstitial pulmonary space (FIG. 6a) as previously described (17). Lungs from all 7 asthmatic mice injected with $SC_{ET}$ pre-loaded with curcumin-coupled nanoparticles were clear of inflammatory pathology as judged by the absence of inflammatory cell types in the pulmonary tissue observed (FIG. 6b). These results suggest that $SC_{ET}$-delivered curcumin nanocomplexes decrease asthmatic inflammation.

The results showed that following IV injection into the mouse, pre-labeled isolated rat Sertoli cells pre-loaded with nanoparticles became entrapped in the host's lungs and were not detected in other tissues and organs, such as the kidneys, thymus and liver. At 15 minutes post-injection, 70% of the labeled nanoparticle load was present in the lungs with some minimal label detection in the liver and kidney, but none in other tissues and organs assayed. Also at 15 minutes post-injection, the pre-loaded, pre-labeled extra-testicular Sertoli cells ($SC_{ET}$) appeared intact based on the unique florescent imaging of these cells, and they appeared to occupy a peri-alveolar distribution throughout the intact lung. However, at one hour post-injection, there was no evidence of intact $SC_{ET}$ in the lungs, although the volume of nanoparticles in the lungs remained at 70% of the total load delivered. By one hour-post injection, it $SC_{ET}$ in the lungs failed to exist as structurally intact cells based on the absence of fluorescent images unique to intact cells and the absorbance quantification of cell specific label. Apparent lysis of the $SC_{ET}$ in the lungs was supported by the electron microscopic detection of cellular debris in pulmonary capillaries. Based on this and the detection and quantification of the nanoparticle specific label in the lungs, these results indicate that the i.v. injected pre-loaded rat $SC_{ET}$ carried and then effectively delivered most (70%) of pre-loaded nanoparticles into and throughout the lungs. The actual targeting of a drug to the lungs in this animal model of pulmonary pathology was verified by the efficient delivery of curcumin (80%) throughout the pulmonary tissue, after which a conspicuous therapeutic effect was noted. Although a dosing protocol was not attempted in this study, the ability to easily deliver an optimal amount of drug to the deep lung, especially to the peri-alveolar sac vasculature by a minimally invasive protocol, is a significant improvement over current drug delivery methodologies.

As illustrated by the results of this invention, the use of $SC_{ET}$ to efficiently deliver therapeutic nanoparticles to the lungs by i.v. injection is an effective alternative to the limitations inherent in the oral route. The delivery of 70% of the nanoparticle load to and throughout the lungs by $SC_{ET}$ compared to the delivery of 10-30% of the load by inhalers to primarily large airways segments of the lung is a significant improvement in drug utilization and may allow for a more efficacious dosing regime.

Discussion and generalizations. Due to increasing mortality from lung diseases, pulmonary drug delivery methods are becoming a common therapeutic approach (Temelkovski 2008). In the cases of asthma and COPD, chitosan nanoparticles have been used to deliver drugs nasally as a viable therapeutic treatment protocol for these debilitating diseases (Sung J. C., Pulliam B. L., & Edwards D. A. Nanoparticles for drug delivery to the lungs. *Trends Biotechnol.*, 25 (12), 563-70 (2007). This novel cell-mediated protocol to target an organ with therapeutic drugs optimizes delivery and retention of nanoparticles into and thoughout the lungs without obvious complications.

The results indicate utilizing xenogeneic Sertoli offer a safe and effective therapeutic protocol for the effective delivery of drug-specific nanoparticles to the lungs to treat pulmonary inflammation, or other pulmonary conditions such as emphysema, asthma and as lung cancer. The mechanism of drug delivery by Sertoli cells is unknown. It is presumably due to the fact that the ~35 micron sertoli cells rupture in the in the lung capillaries, which have a diameter of about 5 microns due to capillary wall pressure. The use of human $SC_{ET}$ cells is not practical so a protocol of this type will require the use of xenogeneic $SC_{ET}$ (such as porcine Sertoli cells) challenging the current reluctance to allowing xenogeneic cell transplantation of any type. Xenogeneic $SC_{ET}$ have been used, without complications, in many discordant cell transplantation protocols (Emerich 2003; Yang W., Peters J. I., & Williams R. O. Inhaled nanopartlices—a current review. Int J Pharm. 356, 239-47 (2008); Yang H., Al-Jazaeri, A, & Wright R. The immunoprotective effects of Sertoli encapsulated islets xengrafts is not dependant upon FAS ligand expression. Cell Transplant. 11, 788-801 (2002); Wang D. Z., et al. Xenotransplantation of neonatal porcine islets and Sertoli cells into nonimmunosuppressed streptozotocin-induced diabetic rats. Transplant. Proc. 37, 470-471 (2005); Dufour J. M., Rajotte R. V., Korbutt G. S., & Emerich D. F. Harnessing the immunomodulatory properties of Sertoli cells to enable xenotransplantation in type I diabetes. Immunol Invest. 32, 275-97 (2003); Cardona K. et al. Long-term survival of neonatal porcine islets in non-human primates by targeting costimulatory pathways. Nature Med. 12(3), 304-306 (2006)) including non-human primates (Dufour J. M., Rajotte R. V., Korbutt G. S., & Emerich D. F. Harnessing the immunomodulatory properties of Sertoli cells to enable xenotransplantation in type I diabetes. *Immunol Invest.* 32, 275-97 (2003)). In the latter study, transfer of deleterious porcine viruses or pathogens by either the transplanted porcine $SC_{ET}$ or isolated pig islets was not detected in the non-human primate hosts although the animals were aggressively evaluated for them (Cardona K. et al. Long-term survival of neonatal porcine islets in non-human primates by targetingcostimulatory pathways. *Nature Med.* 12(3), 304-306 (2006). Alternatively, one can visualize use of non-immunogenic and biocompatible, pressure-sensitive biomaterials replacing the sertolli cells for intravenous delivery of drugs to the deep lung.

The chitosan nanoparticles have been found to be promising carriers for sustained drug release for up to 96 hours (Kumar M. et al. Chitosan IFN-γ-pDNA nanoparticle (CIN) therapy for allergic asthma. *Genet Vaccines Ther.* 1 (Kevin Corkery. Inhalable Drugs for Systemic Therapy. Respir.

Care. 45 (7), 831-835 (2000)), 3 (2003)). There are several administration routes for nanoparticle treatments including, parenteral, oral, intraocular, transdermal and inhalation (Jain D. & Banergee R. Comparison of ciprofloxacin hydrochloride-loaded protein, lipid, and chitosan nanoparticles for drug delivery. *J Biomed Mater Res B Appl Biomater*. 86B (Kevin Corkery. Inhalable Drugs for Systemic Therapy. Respir. Care. 45 (7), 831-835 (2000), 105-112 (2007). The goal of inhaler devices is to deliver most of the therapeutic compound to the central lung and avoid depositions in the oral pathways. However, the aerosol depositions are dependent on breathing pattern, particle size, and airway geometry; which result in low lung disposition and high oropharyngeal disposition (Azarmi S., Roa W. H, & Löbenberg R. Targeted delivery of nanoparticles for the treatment of lung diseases. *Adv Drug Deliv Rev*. 60, 863-75 (2008); Kleinstreuer C., Zhang Z., & Donohue J. F. Targeted drug-aerosol delivery in the human respiratory system. *Annu Rev Biomed Eng*. 10, 1-26 (2008)). The use of nanoparticle transporters in these inhaler devices is also limited due to particle aggregation and their exhalation after inspiration (Newman S. P. Inhaler treatment options in COPD. *Eur Respir Rev*. 14, 102-108 (2005).

A number of additional nanoparticles have been used for in vivo delivery of drugs and genes including a variety of biocompatible polymers other than chitosan such as polyethylene imine (PEI) and/or PLGA (Kircheis, R., et al., Design and gene delivery activity of modified polyethylenimines. Advanced drug Deliv Rev. 2001 Dec. 31; 53(3):341-58; Avgoustakis K. Pegylated poly(lactide) and poly(lactide-co-glycolide) nanoparticles: preparation, properties and possible applications in drug delivery. Curr Drug Deliv. 2004 October; 1(4):321-33), all of which may be used in conjunction with Sertoli Cells.

Curcumin was used in the above examples as a model drug. Depending upon the biomaterials used for drug delivery, a number of drugs such as small molecular chemotherapeutics, petides, proteins, including antibodies, and polynucleotide drugs such as antisense oligonucleotides, small interfering RNAs and microRNAs and plasmids may also be used as drugs. For example chitosan has been used as a carrier of multiple drug types (Tan M L et al doxorubicin delivery systems based on chitosan for cancer therapy. J Pharm Pharmacol. 2009 February; 61(2):131-42; Prabaharan M. chitosan derivatives as promising materials for controlled drug delivery. J Biomater Appl. 2008 July; 23(1): 5-36; Shoyele S A. Controlling the release of proteins/peptides via the pulmonary route. Methods Mol Biol. 2008; 437:141-8).

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A composition comprising a plurality of Sertoli cells loaded with a plurality of chitosan nanoparticles coupled to a compound of interest, wherein the compound is a therapeutic agent.

2. The composition of claim 1, wherein the therapeutic agent is curcumin.

3. The composition of claim 1, further comprising a fluorescent marker bound to the plurality of chitosan nanoparticles.

4. The composition of claim 1, further comprising a fluorescent marker bound to the plurality of Sertoli cells.

5. The composition of claim 1, wherein the Sertoli cells are isolated from mammalian testes.

6. The composition of claim 1, wherein the Sertoli cells are human Sertoli cells.

* * * * *

UNITED STATES PATENT AND TRADEMARK OFFICE
CERTIFICATE OF CORRECTION

PATENT NO. : 10,272,053 B2
APPLICATION NO. : 14/879649
DATED : April 30, 2019
INVENTOR(S) : Arun Kumar, Shyam S. Mohapatra and Don F. Cameron Page 1 of 1

It is certified that error appears in the above-identified patent and that said Letters Patent is hereby corrected as shown below:

In the Specification

Column 7
Line 4, "AlexaFlour" should read --AlexaFluor--.

Column 7
Line 42, "AlexaFlour" should read --AlexaFluor--.

Column 7
Lines 45-46, "AlexaFlour" should read --AlexaFluor--.

Column 7
Line 61, "AlexaFlour" should read --AlexaFluor--.

Column 8
Line 52, "Others" should read --Other--.

Column 8
Line 55, "later evaluated" should read --later and evaluated--.

Column 9
Line 6, "curcumn" should read --curcumin--.

Column 11
Line 1, "(2000))," should read --(2000),--.

Signed and Sealed this
Nineteenth Day of November, 2019

Andrei Iancu
*Director of the United States Patent and Trademark Office*